United States Patent [19]

Devlin

[11] 4,309,207

[45] Jan. 5, 1982

[54] PLANT GROWTH INHIBITING AND ANTIFUNGAL EXTRACT PREPARED FROM THE VEGETATIVE PARTS OF PLANTS OF THE GENERA VACCINIUM AND MYRICA

[76] Inventor: Robert M. Devlin, 157 Bristol Ave., Hyannis, Mass. 02601

[21] Appl. No.: 110,267

[22] Filed: Jan. 7, 1980

[51] Int. Cl.$^3$ ............................................. A01N 65/00
[52] U.S. Cl. .......................................... 71/79; 71/65; 424/364
[58] Field of Search ....................... 71/79, 65; 424/364

[56] References Cited

PUBLICATIONS

Swartz et al., Chem. Abst., vol. 69, (1968), 104039y.

*Primary Examiner*—Catherine L. Mills
*Attorney, Agent, or Firm*—H. G. Jackson

[57] ABSTRACT

There is provided a plant growth inhibiting and antifungal extract prepared from the leaves and/or vines of plants of the genera Vaccinium and Myrica. There is also provided a method for the preparation of the above-said biologically active extract.

10 Claims, No Drawings

PLANT GROWTH INHIBITING AND ANTIFUNGAL EXTRACT PREPARED FROM THE VEGETATIVE PARTS OF PLANTS OF THE GENERA VACCINIUM AND MYRICA

SUMMARY OF THE INVENTION

This invention relates to a method for preparing a biologically active extract from the leaves, particularly the live dormant leaves, and/or vines of plants of the genera Vaccinium (which includes Cranberry and blueberry) and Myrici (which includes bayberry).

This invention also relates to a method for inhibiting the germination of plant seeds and the development of root systems of seedling plants by applying to said seeds or to soil in which the root systems of said seedling plants are growing, a plant growth inhibiting amount of an extract prepared from the leaves and/or vines of cranberry, blueberry or bayberry.

This invention further relates to a method for inhibiting the growth of fungi and/or protecting crops from attack by pathogenic fungi. The method comprises contacting said fungi, and/or applying to the foliage of crops which are to be protected against attack from said pathogenic organisms, a fungicidally effective amount of an extract prepared from the leaves and/or vines of cranberry, blueberry or bayberry.

The plant growth regulating and antifungal extract of the present invention can, as indicated above, be prepared from the leaves and/or vines of cranberry, blueberry and bayberry plants. However, in practice it is preferable to prepare the biologically active extract from live dormant cranberry leaves of the plant species *Vaccinium oxycoccos* or *Vaccinium macrocarpon*. Although the chemical identity of the plant growth regulating and fungicidally effective component(s) of the extract of the present invention has not yet been determined, I have found that the biologically active chemical(s) is present in especially high concentration in live dormant cranberrry leaves. The extraction and partitioning process of the present invention is, therefore, hereinafter discussed in terms of extraction of the active ingredient(s) from live dormant cranberry leaves even though said process is effective for the treatment of green leaves or vines of any of the above-mentioned plants.

In accordance with the process of this invention, live dormant cranberry leaves are placed in a large commercial blender. An aqueous-acetone mixture 20% $H_2O$, 80% acetone, is added and the mixture homogenized. The homogenate is then stored for 3 days at 4° C. and stirred several times to facilitate extraction. The homogenate is then filtered, preferably twice, through glass wool (or cheesecloth) and Whatman No. 1 filter paper. The acetone is then evaporated off in a flash evaporator at 45° C. and the remaining fraction filtered, preferably twice, through cheesecloth and Whatman No. 1 filter paper. After adjusting the pH of the extract to 2 with concentrated sulfuric acid, said extract is then transferred to a separatory vessel and extracted, preferably twice, with ethyl acetate. The extracts are combined and placed in another separatory vessel and extracted, preferably twice, with a 5% aqueous-sodium bicarbonate solution. The organic phases are discarded. The aqueous phases are combined, acidified to pH 2 with concentrated sulfuric acid, and extracted, preferably twice, with ethyl acetate. The organic layers are transferred to a flash evaporator and the solvent evaporated at 45° C. The dry residue is dissolved in water and stored at 4° C. During storage a yellow precipitate forms which can be removed by filtration, centrifugation or the like. The clear brown supernatant, remaining after separation of the yellow precipitate, is highly effective as both an anti-fungal agent and a plant growth inhibitor.

The potency of this extract, determined on an activity per unit weight basis, can be further enhanced by treatment of said extract as follows: (1) concentrate said extract in vacuo and warm the resulting residue in dilute hydrochloric acid, (2) filter and add water to the acidified extract and treat the aqueous acidified extract with ethyl acetate, (3) separate the ethyl acetate from the aqueous phase and wash said ethyl acetate extract with brine and then with a 5% aqueous sodium bicarbonate solution, (4) separate the sodium bicarbonate extract from the ethyl acetate fraction and evaporate the ethyl acetate from said ethyl acetate fraction. The remaining residue is dissolved in water and provides a plant growth regulating and fungicidally effective extract which, on an activity per unit weight basis, is three times more effective than the crude extract employed as starting material.

Additionally, I have also found that further treatment of the sodium bicarbonate fraction from the above procedure yields an extract which is eight times more effective, on an activity per unit weight basis, than the crude extract used as starting material for the above-extraction process. This treatment involves:

(1) the acidification of the sodium bicarbonate fraction from the above procedure, to pH 1 using concentrated hydrochloric acid, (2) extraction of said acidified sodium bicarbonate fraction with ether, (3) separation of the ether layer from the acidic solution and (4) evaporation of the ether from the separated ether fraction to yield a residue which is dissolved in water to provide the highly effective plant growth regulating and fungicidally effective extract.

EXAMPLE 1

Preparation of Cranberry leaf extract and evaluation of said extract as a plant growth inhibitor A 200 g sample of live dormant cranberry (genus Vaccinium) leaves was blended for 3 minutes at high speed with 1500 ml of 80% acetone. For this purpose a large stainless steel commercial Blendor was used. The homogenate was poured into a 2000 ml Erlenmeyer flask and stored for 48 hours at 4° C. During storage the homogenate was stirred several times to facilitate extraction. The homogenate was then filtered twice through glass wool (or cheesecloth) and Whatman No. 1 filter paper without suction. The acetone was evaporated off in a flash evaporator at 45° C. and the remaining fraction filtered twice through cheesecloth and Whatman No. 1 filter paper. After adjusting the pH to 2 with concentrated sulfuric acid, the crude extract (about 250 ml) was then transferred to a 1000 ml separatory funnel and extracted twice for one minute with 200 ml portions of ethyl acetate. The combined extracts were then transferred to another 1000 ml separatory funnel and extracted twice for one minute with equal portions of a 5% sodium bicarbonate solution. The organic phases were discarded. The combined aqueous phases were acidified to pH2 with concentrated sulfuric acid and extracted twice for one minute with equal portions of ethyl acetate. The combined organic layers were transferred to a flash evaporator and the solvent evaporator at 45° C. The dry residue is redissolved in 20 ml of water and stored at 4° C. The above procedure was repeated several times until enough extract was accumulated to accommodate the experiments planned. During storage a yellow precipitate appears. The precipitate is removed by centrifugation at 10° C. and 4000 rpm for 10 minutes. The clear brown supernatant was tested for growth regulator properties using the following protocol.

Wheat (*Triticum aestivum L.*) seeds were sown in 5 cm diameter paper dixie cups (25 seeds per cup) that contained moist vermuculite. The seeds were placed on the pressed surface of the vermiculite and then covered with a one cm layer of moist vermiculite. The covering layer was gently pressed down and leveled. The bottom of the cup was punctured several times to allow for good drainage. Leaf extract was applied in water to the pressed vermiculite surface, using a small bulb atomizer. In each treatment 10 ml of liquid was applied to each cup. There was a total of four treatments: (a) 10 ml $H_2O$, (b) 9 ml $H_2O$ plus 1 ml extract, (c) 5 ml $H_2O$ plus 5 ml extract, and (d) 10 ml extract. The bottom half of a petri dish was placed under each cup to collect any excess drainage. Each treatment was replicated 4 times. The treated seeds were then transferred to an incubator and kept in the dark for 3 days under a constant temperature of 25° C. During this time the germinating seeds were loosely covered with a sheet of plastic to keep humidity high. After 3 days the germinating seeds were transferred to a growth chamber where constant condition of light (white, 10.8 klux, 20 hr light and 4 hr dark) and temperature (25±1° C.) were maintained. Eight high-output flourescent lamps (F48T 12-CW-HO) and four 60-W incandescent light bulbs provided the light source. While in the growth chamber the plants were watered daily (when needed) by pouring water into the containing petri dish half. After 7 days of growth (3 in the incubator and 4 in the growth chamber) the ten longest seedlings from each cup were collected and their average shoot and root lengths determined. With this method of selection, treatment effects, if they exist, are more visible. The number of seeds that actually germinated was also determined. Since treatments were replicated 4 times, each data point in length measurements represents the mean of 40 plants. Data obtained are reported in Table I below.

TABLE 1

Effect of cranberry leaf extract on the germination, root length, and shoot length of wheat.

| Extract (ml) | Average No. of Seeds Germinated | Average Shoot Length (mm) | Average Root Length (mm) |
|---|---|---|---|
| 0 | 25.0 | 102.1 | 66.4 |
| 1 | 24.0 | 87.4 | 57.5 |
| 5 | 14.3 | 17.2 | 15.2 |
| 10 | 7.5 | 7.5 | 7.6 |

From this data it can be seen that no significant decrease in germination was observed in those seeds receiving only 1 ml of extract. However, when 5 ml of extract was applied there was a 42% decrease in germination and with 10 ml a 70% decrease.

In addition to inhibiting germinating, growth of those seeds that did germinate was severely retarded. When 1 ml of extract was applied there was a 13% decrease in root length and a 14% decrease in shoot length (Table 1). Growth retardation was dramatic when applications of extract were increased to 5 and 10 ml. Treatment of seeds with 5 ml of extract caused a 77% decrease in root length and an 83% decrease in shoot length (Table 1). An 88% decrease in root length and a 93% decrease in shoot length was observed in those seedlings treated with 10 ml of leaf extract.

The above procedure was repeated excepting that 200 g of cranberry vines and leaves were extracted with 80% acetone and partitioned following the same procedures used for the leaves. Wheat seeds used for the germination and growth response evaluations, as described above, were placed on the pressed surface of moist vermiculite and covered with a cm layer of moist vermiculite. The covering layer was gently pressed down and leveled and the bottom of the cup, in which the seeds were planted, was punctured several times to provide good drainage. The vermiculite surface was then sprayed with 10 ml of water or 10 ml of vine and leaf extract. The treated cups were then incubated for 3 days and placed in a growth chamber for four days. The handling procedures were as described above and the results were essentially similar to those obtained with the extract of dormant cranberry leaves. Controls germinated and grew normally; whereas, germination of seeds treated with 10 ml of the extract was severely inhibited and root growth thereof markedly diminished.

The above procedures were again repeated, excepting that radish seeds were used as the plant species for germination and root and shoot growth evaluation. Biological responses obtained with the radish seeds were essentially the same as those obtained with wheat. Radish seeds treated with cranberry extract showed marked decreases in germination, root growth and shoot growth.

EXAMPLE 2

Preparation of cranberry leaf extract and evaluation of said extract as a plant growth Inhibitor The extraction procedure of Example 1 was repeated, excepting that the homogenate from the aqueous-acetone extraction of the live dormant cranberry leaves was allowed to stand for 72 hours rather than 48 hours before separating the extraction fluids from the vegetative solids. The extract obtained was worked up as described in Example 1 above, and bioassayed by the following procedure.

Wheat (*Triticum aestivum L.*) seeds were sown in 5 cm diameter paper dixie cups (25 seeds per cup) that contain moist vermiculite. The seeds were placed on the pressed surface of the vermiculite and then covered with a one cm layer of moist vermiculite. The covering layer was gently pressed down and leveled. The bottom of the cup was punctured several times to allow for good drainage. Leaf extract was applied in water to the pressed vermiculite surface, using a small bulb atomizer. In each treatment 10 ml of liquid was applied to each cup. There were a total of three treatments: (a) 10 ml $H_2O$, (b) 5 ml $H_2O$ plus 5 ml extract and (c) 10 ml extract. The bottom half of a petri dish was placed under each cup to collect any excess drainage. Each treatment was replicated 4 times. The treated seeds were then transferred to an incubator and kept in the dark for 3 days under a constant temperature of 25° C. During this time the germinating seeds were loosely covered with a sheet of plastic to keep humidity high. After 3 days the germinating seeds were transferred to a growth chamber where constant conditions of light (white, 10.8 klux, 20 hr light and 4 hr dark) and temperature (25±1° C.) were maintained. Eight high-output fluorescent lamps (F48T 12-CW-HO) and four 60-W incandescent light bulbs provided the light source. While in the growth chamber the plants were watered daily (when needed) by pouring water into the containing petri dish half. After 7 days of growth (3 in the incubator and 4 in the growth chamber) the ten longest seedlings from each cup were collected and their average shoot and root lengths determined. With this method of selection treatment effects, if they exist, are more visible. The number of seeds that actually germinated was also determined. Since treatments were replicated 3 times, each data point in length measurements represents the mean of 30 plants. Data obtained are reported in tables II and III below.

TABLE II

Effect of Cranberry leaf extract on seed Germination-Evaluations using 25 wheat seeds per cup
No. of Seeds Germinated

| Replicates | Treatment | Treatment B | Treatment C |
|---|---|---|---|
| 1 | 19 | 20 | 3 |
| 2 | 24 | 16 | 2 |
| 3 | 18 | 19 | 1 |

TABLE III

Effect of Cranberry leaf extract on Root length and Shoot length of wheat

| | Treatment A | | Treatment B | | Treatment C | |
|---|---|---|---|---|---|---|
| Replicates | Root length | Shoot length | Root length | Shoot length | Root length | Shoot length |
| 1 | 7.9 | 10. | 4.9 | 4.1 | 1.9 | 1.0 |
| 2 | 9.6 | 11.7 | 5.3 | 4.6 | 1.5 | 0.8 |
| 3 | 8.6 | 10.7 | 4.8 | 3.6 | 1.9 | 0.6 |
| Average | 8.7 | 10.9 | 5 | 4.1 | 1.8 | 0.8 |

From the above data it can be seen that seed germination, as well as, root growth and shoot growth were markedly reduced by the application of cranberry extract to planted wheat seeds.

The above described bioassay procedures were used to determine whether cranberry extract obtained from live green cranberry leaves also exhibits plant growth inhibiting activity. For this determination the extract from green cranberry leaves was prepared by the procedure described in Example 1. The results of the bioassay show that wheat seeds employed as controls (i.e. those treated with 10 ml $H_2O$) germinated and grew normally. Seeds treated with 5 ml $H_2O$ and 5 ml of the green cranberry leaf extract showed a reduced germination and a reduction in both root length and shoot length. Seeds treated with 10 ml of green cranberry leaf extract showed a marked reduction in seed germination as well as a marked reduction in both root growth and shoot growth.

EXAMPLE 3

Preparation of Blueberry leaf extract and evaluation of said extract as a plant growth Inhibitors The procedures of Example 1 were followed excepting that 200 g of blueberry (genus Vaccinium), leaves were used to prepare the extract. The extract was worked up in the same manner described in Example 1 above, and the wheat germination and root growth and shoot growth evaluations were also made by the procedures described in said example. Controls (i.e. wheat seeds treated with 10 ml $H_2O$) germinated and grew normally. Seeds treated with 5 ml $H_2O$ and 5 ml of blueberry extract germinated 2 days later than controls and grew less vigorously than controls. Seeds treated with 10 ml of blueberry extract germinated 4 days later than the controls and developed at a much less vigorous pace than both the controls and the seeds treated with 5 ml $H_2O$ and 5 ml extract.

EXAMPLE 4

Preparation of Bayberry leaf extract and evaluation of said extract as a plant growth Inhibitor The procedures of Example 1 were again repeated excepting that 200 g of bayberry (Myrica pensylvania) leaves were used to prepare the extract.

The extract was worked up in the same manner described in Example 1 above, and the wheat germination and root growth and shoot growth evaluations were likewise conducted in the manner described. Wheat seeds used as controls (i.e. treated with 10 ml $H_2O$) germinated and grew normally. Seeds treated with 5 ml of $H_2O$ and 5 ml of extract germinated 3 days later than controls. Germination rate was slightly less than controls and plants were shorter than controls. Seeds treated with 10 ml of bayberry extract germinated 5 days after controls and the germination rate was much lower than controls. Shoot growth was considerably less than controls.

EXAMPLE 5

Determination of antifungal activity of Cranberry leaf extract

The effectiveness of Cranberry leaf extract as an antifungal agent was demonstrated when wheat seeds from the seed germination test, as described in Example 1, were placed on a greenhouse bench for a 4 day holding period. A heavy fungal infestation developed on the untreated control, whereas, treated samples were free of fungus infestation.

To confirm this finding, cranberry extract, prepared in accordance with the procedure of Example 1, was partitioned by thin layer chromatography (TLC) with the following solvents: benzene, methanol and glacial acetic acid (90:16:8). The bands were scraped from the TLC plate and eluted with water. The solutions, thus prepared, were used to treat wheat seeds. Fifteen seeds per treatment were placed on two pads of Whatman No. 1 filter paper placed in small dishes. The seeds were then covered with two pads of Whatman No. 1 filter paper and treated with 1 ml of eluate; then placed in a dark cabinet and held at 25° C. for four days. At the end of the holding period all samples were examined for seed germination, plant growth of germinated seeds and antifungal activity. The pH of the bands on the TLC plate which were eluted, are as follows:

1=5.13, 2=5.11, 3=5.3, 4=5.3, 5=5.13, 6=5.3, 7=5.11, 8=5.32, 9=5.7, 10=4.99, 11=5.17 and 0=5.03. In this evaluation 0 represents the untreated control. Data obtained are reported below in table IV.

TABLE IV

Antifungal activity of Cranberry leaf Extract

| Treatment No. | Band pH | % Seed Germination | Plant growth of Germinated Seeds | Fungus Growth |
|---|---|---|---|---|
| 0 | 5.03 | 70 | normal | Heavy |
| 1 | 5.13 | 50 | normal | Heavy |

TABLE IV-continued

Antifungal activity of Cranberry leaf Extract

| Treatment No. | Band pH | % Seed Germination | Plant growth of Germinated Seeds | Fungus Growth |
| --- | --- | --- | --- | --- |
| 2 | 5.11 | 30 | normal | Heavy |
| 3 | 5.3 | 100 | retarded | Heavy |
| 4 | 5.3 | 70 | normal | Heavy |
| 5 | 5.13 | 40 | slightly retarded | None |
| 6 | 5.3 | 40 | normal | Heavy |
| 7 | 5.11 | 70 | slight stimulation | Heavy |
| 8 | 5.32 | 33 | slightly retarded | Heavy |
| 9 | 5.17 | 50 | slight stimulation | Heavy |
| 10 | 4.99 | 60 | retarded | Heavy |
| 11 | 5.17 | 50 | normal | None |

From these data it can be seen that the eluate from the bands 5 and 11 inhibited fungal development.

EXAMPLE 6

Preparation of Cranberry leaf extract and evaluation of said extract as a plant growth Inhibitor The cranberry leaf extract utilized in the following evaluation was prepared in the manner and by the procedure of Example 1. The resulting extract was evaluated by the procedure described below.

BIOASSAY

Evaluation of Cranberry Leaf Extraction on Wheat and Lettuce Seed Germination and Root Growth Twenty (20) wheat seeds (*Triticum aestivum* var 'Olaf' spring or twenty (20) lettuce seeds (*Letuca sative* var 'Grand Rapids') wheat), where placed between 2 pieces of 9 cm Whatman No. 1 filter paper in 100×15 mm plastic optilux petri dishes. Four (4) mls of the extract solution or serial dilutions thereof made up of 2 ml of extract plus 2 ml of $H_2O$, 1 ml of extract plus 3 ml of $H_2O$ and 0.25 ml of extract plus 3.75 ml $H_2O$, were pipetted into the dish to completely saturate both pieces of paper. Four (4) mls of de-ionized water was used as a check. The covered petric dishes were placed in the dark for approximately 64 hours. They were then removed and the lengths of the primary roots measured. (In initial tests, the lengths of all 20 roots were recorded. However, in subsequent tests, the 5 longest and 5 shortest lengths were eliminated, and the lengths of the 10 most uniform roots were recorded. In some cases, where the roots were too short to be measured accurately, a visual estimation was made). Data obtained are reported in Table V below.

TABLE V

Evaluation of Cranberry leaf extract as a plant growth inhibitor on wheat and Lettuce Seeds

| Treatment | % Inhibition Wheat Germination | Average root length cm | % Inhibition Lettuce Germination | Average root length cm |
| --- | --- | --- | --- | --- |
| 4 ml $H_2O$ | 0 | 2.29 | 0 | 0.67 |
| 4 ml Extract | 100 | — | 100 | — |
| 2 ml Extract + 2 ml $H_2O$ | 30 | 0.22 | 100 | — |
| 1 ml Extract + 3 ml $H_2O$ | 20 | 1.03 | 100 | — |
| 0.25 ml Extract + 3.75 ml $H_2O$ | 5 | 1.92 | 70 | 0.81 |

EXAMPLE 7

Preparation of Cranberry leaf extract and evaluation thereof as a plant growth Inhibitor A 7 ml sample of cranberry leaf extract prepared in accordance with the procedure of Example 6 above was concentrated in vacuo to give a residue weighing 0.62 g. This residue was dissolved in 7.0 ml of 1.0 N HCl and heated for 1 hour at 60° C. The solution was cooled and filtered under vacuum. The resulting precipitate was washed with 10 ml $H_2O$. The filtrates were combined and extracted twice with 17 ml portions of ethyl acetate. The ethyl acetate layers were washed with 8 ml of brine and then 3 times with 2 ml portions of saturated $NaHCO_3$. The ethyl acetate layer was dried over sodium sulfate, filtered, and concentrated to give a residue weighing 40 mg. This residue was dissolved in 7 ml $H_2O$ and bioassayed as described in Example 6. Determinations show that this material was 3.25 times more active, on an activity per unit weight basis, than the initial cranberry leaf extract prepared in Example 6.

The combined sodium bicarbonate layers, from the above procedure, were acidified to pH 1 with concentrated hydrochloric acid and then extracted twice with 13 ml portions of ether followed by two extractions with 13 ml portions of ethyl acetate; these were kept separate and after washing and drying, as described above, gave residues weighing 22 and 45 mg respectively. Each was dissolved in 7 ml of water and bioassayed. The bioassay showed the material from the ether extract to be 8.1 and that from the ethyl acetate extract to be 2.4 times more active than the initial cranberry leaf extract prepared in Example 6 on an activity per unit weight basis.

The bioassay employed in the following evaluations was the same as that described in Example 6, where it was shown that 0.25 ml of cranberry leaf extract plus 3.75 ml of water produced a 5% suppression of wheat germination and a 16.5% reduction in root growth of germinated plants.

Data obtained in the bioassay using wheat seeds are reported in Table VI below.

TABLE VI

Evaluation of Cranberry Leaf Extract on Wheat Seed Germination and Root Growth

| Treatment | % Inhibition of Seed Germination | Average Root length (cm) | % Root length Inhibition |
| --- | --- | --- | --- |
| 4 ml $H_2O$ | 0 | 2.45 | — |
| 4 ml EAL | 10 | 1.34 | 45.3 |
| 2 ml EAL + 2 ml $H_2O$ | 0 | 1.61 | 34.3 |
| 1 ml EAL + 3 ml $H_2O$ | 15 | 2.0 | 18.4 |
| 4 ml EL | 5 | 0.84 | 65.7 |
| 2 ml EL + 2 ml $H_2O$ | 10 | 1.32 | 46.1 |
| 1 ml EL + 3 ml $H_2O$ | 10 | 1.92 | 21.6 |
| 4 ml ELXEAL | 15 | 1.42 | 42.0 |
| 2 ml ELXEAL + 2 ml $H_2O$ | 75 | 1.50 | 38.8 |
| 1 ml ELXEAL + 3 ml $H_2O$ | 5 | 2.20 | 10.2 |

EAL = ethyl acetate layer
EL = ether layer
ELXEAL = ether layer extracted with ethyl acetate

EXAMPLE 8

Preparation of Cranberry leaf extract and evaluation thereof as a plant growth Inhibitor A 3.0 ml sample of cranberry leaf extract prepared by the method of Example 6 above was concentrated to give 235 mg of a dark residue. This residue was dissolved in 3.0 ml of 1.0 N hydrochloric acid and heated at 55°–60° C. for 1 hour. After cooling the solution was centrifuged for 2 minutes and the supernatant decanted from the precipitate.

The supernatant was extracted twice with 3 ml portions of ether. The ether layers were then dried over sodium sulfate, filtered, and concentrated to yield 8 mg of a greenish glassy residue. This residue was dissolved in 4 ml of water and bioassayed. This sample was 5.91 times more active, on an activity per unit weight basis, than the cranberry leaf extract used as the starting material for this preparation.

Extraction of the supernatant from the above treatments with ethyl acetate gave a yellow glassy residue weighing 54 mg, which was then dissolved in 4 ml of water and bioassayed by the procedure described in Example 6. This sample was 1.8 times more active on an activity per unit weight basis than the extract used as starting material herein.

TABLE VII

Evaluation of Cranberry Leaf Extract on Wheat Seed Germination and Root Growth

| Treatment | % Inhibition of Seed Germination | Average Root length (cm) | % Root length Inhibition |
|---|---|---|---|
| 4 ml H$_2$O | 0 | 2.50 | — |
| 4 ml EAL | 5 | 1.12 | 60 |
| 4 ml EL | 0 | 1.89 | 32.5 |

EAL = ethyl acetate layer
EL = ether layer

I claim:

1. A plant growth inhibiting and fungicidally effective extract prepared from the leaves and/or vines of plants of cranberry, blueberry and bayberry by the method comprising: admixing said leaves and/or vines of said plants with an aqueous-acetone mixture, whereby acetone soluble and water soluble chemicals are extracted from said leaves and/or vines, separating the aqueous-acetone extract from the leaf and or vine solids, evaporating the acetone from said aqueous-acetone extract to reduce the volume thereof to approximately 15 to 25 percent of its initial volume, adjusting the pH of the resulting extract to a pH value between 1 and 2 by addition thereto of concentrated sulfuric acid, treating the acidified extract with ethyl acetate and washing the ethyl acetate extract with an aqueous solution of sodium bicarbonate, separating the aqueous mixture from the organic mixture and adjusting the pH of said aqueous mixture to a pH value of from 1 to 2 with concentrated sulfuric acid, admixing ethyl acetate with said acidified aqueous mixture, separating the ethyl acetate extract from the aqueous mixture, evaporating the ethyl acetate from said extract and dissolving the resulting residue in a solvent selected from the group consisting of water and C$_1$-C$_4$ alcohols, whereby the plant growth regulating and fungicidal extract is obtained and the active ingredient is present in an effective amount for inhibiting seed germination, seedling growth and fungus.

2. A plant growth inhibiting extract according to claim 1 wherein said extract is prepared from the live dormant leaves of plants of the genera Vaccinium.

3. A plant growth inhibiting extract according to claim 2 wherein said extract is prepared from live dormant cranberry leaves.

4. A plant growth inhibiting extract according to claim 1 wherein said extract is concentrated in vacuo and the resulting extract warmed in hydrochloric acid filtered and water added to the acidified extract and the resulting aqueous mixture extracted with ethyl acetate, the ethyl acetate is separated from said aqueous mixture, washed with brine and then sodium bicarbonate solution, the ethyl acetate layer is separated from the sodium bicarbonate solution, dried and the ethyl acetate evaporated, the remaining residue is dissolved in water to give the plant growth inhibiting extract.

5. A plant growth inhibiting extract according to claim 4 wherein the sodium bicarbonate solution from the claim 4 extraction is acidified to pH 1 with concentrated hydrochloric acid and the resulting acidified solution extracted with ether, the ether layer is separated from the acid solution and the ether evaporated, the remaining residue is dissolved in water to give the plant growth inhibiting extract.

6. A method for preparing a plant growth inhibiting extract from the leaves and/or vines of plants of the genera Vaccinium and Myrica comprising the steps of (1) admixing said leaves and/or vines of said plants with a 20% by volume water, 80% by volume acetone solution, (2) separating said aqueous-acetone extract from said leaf and/or vine solids, (3) evaporating the acetone to reduce the volume of the aqueous-acetone extract to 15 to 25% of its initial volume, (4) adjusting the pH of the resulting extract a pH value between 1 and 2 by the addition thereto of concentrated sulfuric acid, (5) treating the acidified extract with ethyl acetate and washing the acidified ethyl acetate mixture with an aqueous solution of sodium bicarbonate, (6) separating the aqueous mixture from the ethyl acetate mixture and adjusting the pH of said aqueous mixture to a pH value between 1 and 2 with concentrated sulfuric acid (7) admixing ethyl acetate with the acidified aqueous mixture and separating the ethyl acetate mixture from said aqueous mixture, (8) evaporating the ethyl acetate from said ethyl acetate mixture and dissolving the remaining residue in water and or a lower C$_1$-C$_4$ alkyl alcohol, whereby the plant growth regulating extract is obtained.

7. A method for the preparation of a plant growth inhibiting extract according to claim 6 wherein said extract is concentrated in vacuo and the resulting residue warmed in dilute hydrochloric acid, filtered and water added to the acidified solution and the thus prepared aqueous mixture extracted with ethyl acetate, said ethyl acetate extract is separated from said aqueous mixture and washed with brine and then with sodium bicarbonate solution, the sodium bicarbonate solution is separated from the ethyl acetate extract and the ethyl acetate evaporated, the remaining residue is then dissolved in water to give the plant growth inhibiting extract.

8. A method for the preparation of a plant growth inhibiting extract according to claim 7 wherein the sodium bicarbonate solution from claim 7 is acidified to pH 1 with concentrated hydrochloric acid and the resulting acidified solution extracted with ether, said ether extract is then separated from the acid solution and the ether evaporated, the remaining residue is then dissolved in water to yield the plant growth inhibiting extract.

9. A method for inhibiting the germination of seeds comprising, applying to said seeds an effective amount of an extract of live dormant leaves of Cranberry plants prepared by the process of admixing live dormant cranberry leaves with an aqueous-acetone mixture, whereby acetone soluble and water soluble chemicals are extracted from said leaves, separating the aqueous-acetone extract from the leaf solids, evaporating the acetone from said aqueous-acetone extract to reduce the volume thereof to approximately 15 to 25 percent of its initial volume, adjusting the pH of the resulting extract to a pH value between 1 and 2 by addition thereto of concentrated sulfuric acid, treating the acidified extract with ethyl acetate and washing the acidified ethyl acetate mixture with an aqueous solution of sodium bicarbonate, separating the aqueous mixture from the organic mixture and adjusting the pH of said aqueous mixture to a pH value of from 1 to 2 with concentrated sulfuric acid, admixing ethyl acetate with said acidified aqueous mixture, separating the ethyl acetate extract from the aqueous mixture, evaporating the ethyl acetate from said extract and dissolving the resulting residue in water to obtain the desired extract.

10. A method for protecting agronomic crops from attack by pathogenic fungi comprising, applying to the foliage of said crops a fungicidally effective amount of an extract of live dormant leaves of cranberry plants prepared by the process of admixing said live dormant cranberry leaves with an aqueous-acetone mixture, whereby acetone soluble and water soluble chemicals are extracted from said leaves, separating the aqueous-acetone extract from the leaf solids, evaporating the acetone from said aqueous-acetone extract to reduce the volume thereof to approximately 15 to 25 percent of its initial volume, adjusting the pH of the resulting extract to a pH value between 1 and 2 by addition thereto of concentrated sulfuric acid, treating the acidified extract with ethyl acetate and washing the acidified ethyl acetate mixture with an aqueous solution of sodium bicarbonate, separating the aqueous mixture from the organic mixture and adjusting the pH of said aqueous mixture to a pH value of from 1 to 2 with concentrated sulfuric acid, admixing ethyl acetate with said acidified aqueous mixture, separating the ethyl acetate extract from the aqueous mixture, evaporating the ethyl acetate from said extract and dissolving the resulting residue in water to obtain the desired extract.

* * * * *